Jan. 15, 1963 G. J. MELK ET AL Plant Pat. 2,218

GLADIOLUS PLANT

Filed Feb. 27, 1962

GEORGE J. MELK INVENTORS

GEORGE J. MELK, JR.

BY H. J. Barnett ATTORNEY

United States Patent Office

Plant Pat. 2,218
Patented Jan. 15, 1963

2,218
GLADIOLUS PLANT

George J. Melk and George J. Melk, Jr., both of 10321 N. Wauwatosa Road, Mequon, Wis.

Filed Feb. 27, 1962, Ser. No. 176,169
1 Claim. (Cl. 47—60)

Our present invention relates to a new and improved variety of gladiolus plant and is notable particularly for its size, number of buds simultaneously showing color, and vigorous, tall spikes of uniform field height.

To the best of our knowledge, this new variety is the result of a cross between the varieties Spic and Span (unpatented) and Margery (unpatented). Spic and Span is the seed parent and Margery is the pollen parent. Hand cross-pollination was done by us in our field at Mequon, Wisconsin, but no precaution was taken to prevent admixture of other varieties by bees and insects.

This new variety has been asexually reproduced by us in our fields at Mequon, Wisconsin, by natural increase from cormels through several generations, and its characteristics have proven to be permanently fixed.

The illustration, made a part of this application, shows two views of this variety.

Figure 1:
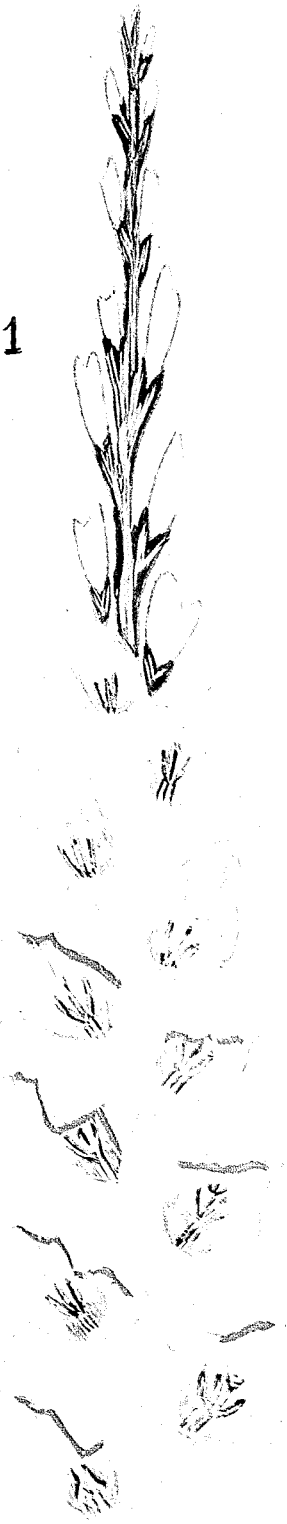
FIG. 1 is a single bloom spike of this new variety, as nearly true to color as is possible.
Figure 2:
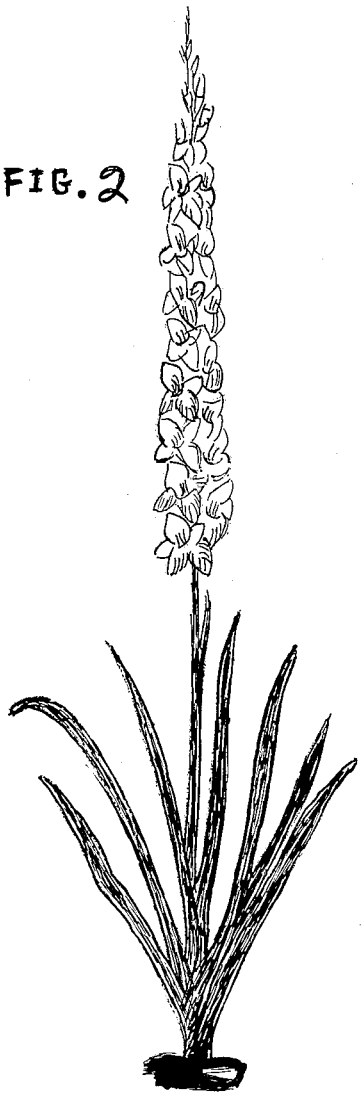
FIG. 2 is a pen and ink drawing showing the general shape and proportion of the plant relative to the spike. The illustration shows the shape and symmetry of the spike, as well as the distinctive pink coloring.

In the following detailed description, color references indicate "Ridgway's Color Standards of 1912." Where there are other references to color, the ordinary dictionary meanings of the terms are intended.

*Plant*

Growth: Very vigorous; very tall, blossom spike usually attaining a height of 65–75 inches. Propagation is good.

Blooming: Each spike generally has a total of 22–26 buds and flowers, with 8–12 being open at one time, while 7–9 additional unopened buds show color. When the first floret opens, the buds are proportionately and evenly spaced, and all but the top 3–4 buds on the spike show color. This variety will bloom in about 75 days from date planted from large bulbs.

Foliage: Deep green. Relatively short plant, wide at the base, 7 leaves. Upright; 20–28 inches high. Average leaf 2 inches wide.

Stems: Usually straight and hard. Diameter at base is ½ to ¾ inch. The stem, including that part from the first bud upward, is more fibrous than most existing varieties, thereby facilitating better packing and handling with less breakage of the spike.

Disease resistance: This variety has been found unusually resistant to various diseases such as Botrytis, Fusarium rot, and Sclerotina dry rot, when grown in a loam soil in our fields at Mequon, Wisconsin, under the natural conditions of the climate of the area. At the end of the season, it would be found that many other varieties and seedlings had succumbed or had been badly affected by the various diseases, whereas this variety remained healthy and unaffected. In our field in Mequon, Wisconsin, this variety has proved to be hardy under adverse climate conditions. For example, the stem does not crook, nor do the flowers and spikes sustain damage from extreme heat and sun.

Corms: This variety produces round and well husked bulbs. The husks have a deep rose cast. The flesh is deep yellow.

*Flower*

Spike: Long and slender; 22–26 buds of which 1–5 open on the first day, following which 8–10 are open on the second day, following which 10–12 are open at one time until all the buds have opened. About 7–9 buds will show color at one time.

Bud: Opening buds are 2½ to 3½ inches long.

Arrangement: Florets are formally disposed in a double row on the spike, and usually all face forward.

Size: Individual florets usually measure from 4 inches to 5 inches across. Upper blooms are progressively smaller.

Form: Flowers are wide open, gently curved, and usually round. Edges of petals are delicately ruffled.

Petal size: The outer petals are 1¾ to 2¼ inches in diameter, and the inner petals are 1¼ to 2 inches in diameter.

Substance: Heavy; surface smooth with some petals creased at the center toward the tips.

Fragrance: None.

Color: The colors in "Ridgway's Color Standards of 1912" which most closely resemble our variety are as follows: buds are Shrimp Pink (Plate I); inside surfaces of florets are Hermosa Pink (Plate I) and La France Pink (Plate I), fading to Cameo Pink (Plate XXVI) as the blooms age; and the throats shade to Thulite Pink (Plate XXVI), occasionally etched with Magenta (Plate XXVI).

Reproductive organs:

*Stamens.*—Dull dusky purple.

*Pistils.*—White.

*Comparisons*

Our new variety resembles Traveler (unpatented) more than any other known variety, but differs from it principally as follows:

(1) Our variety is much taller than Traveler under normal growing conditions.

(2) Our variety has more buds showing color at one time than Traveler.

(3) Our variety has a more uniform field height than Traveler.

(4) Our variety has a taller stem than Traveler. The stem of our variety is willowy and hard, and can be cut more easily without damage to the foliage.

(5) Our new variety has a greater color contrast between the open florets and the buds showing color than Traveler.

Having thus disclosed our invention, we claim:

The new variety of gladiolus plant, substantially as herein described and illustrated, characterized by its unusual color, uniform field height, low wide foliage, straightness of stem, and superior bulb producing ability.

No references cited.